(12) United States Patent
Grube et al.

(10) Patent No.: US 9,771,081 B2
(45) Date of Patent: Sep. 26, 2017

(54) SYSTEM FOR FATIGUE DETECTION USING A SUITE OF PHYSIOLOGICAL MEASUREMENT DEVICES

(71) Applicant: THE BOEING COMPANY, Chicago, IL (US)

(72) Inventors: Robert William Grube, Edmonds, WA (US); Lisa C. Thomas, Kirkland, WA (US); Kimberly Marie Craig, Everett, WA (US); Christopher Marc Gast, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 31 days.

(21) Appl. No.: 14/500,264

(22) Filed: Sep. 29, 2014

(65) Prior Publication Data

US 2016/0090097 A1    Mar. 31, 2016

(51) Int. Cl.
| | | |
|---|---|---|
| *B60W 40/08* | (2012.01) | |
| *G08B 21/06* | (2006.01) | |
| *A61B 5/18* | (2006.01) | |
| *A61B 5/00* | (2006.01) | |

(52) U.S. Cl.
CPC ............. *B60W 40/08* (2013.01); *A61B 5/18* (2013.01); *A61B 5/7264* (2013.01); *G08B 21/06* (2013.01); *B60W 2040/0827* (2013.01)

(58) Field of Classification Search
CPC .... B60W 40/08; A61B 5/0022–5/0024; A61B 5/02438; A61B 5/1112; A61B 2560/0209; A61B 5/18; G08B 21/06
See application file for complete search history.

(56) References Cited

U.S. PATENT DOCUMENTS

| | | | | |
|---|---|---|---|---|
| 7,027,621 B1* | 4/2006 | Prokoski | ............ | G06K 9/00255 180/272 |
| 8,289,172 B2 | 10/2012 | Matos | | |
| 2005/0192730 A1* | 9/2005 | Churchill | ............... | G08G 1/164 701/45 |
| 2007/0296601 A1* | 12/2007 | Sultan | ...................... | A61B 5/18 340/576 |

(Continued)

OTHER PUBLICATIONS

Sayette, et. al., "A Psychometric Evaluation of the Facial Action Coding System for Assessing Spontaneous Expression", Journal of Nonverbal Behavior, vol. 25, pp. 167-186. [Available Online] http://www.ri.cmu.edu/pub_files/pub3/sayette_m_a_2001_1/sayette_m_a_2001_1.pdf.

(Continued)

*Primary Examiner* — Orlando Bousono
(74) *Attorney, Agent, or Firm* — Patterson + Sheridan, LLP

(57) ABSTRACT

A system, method, and computer program product for detecting, in real time, a fatigue level of a vehicle operator. Multiple physiological indicators of an individual vehicle operator can be monitored at different instances when the operator's level of fatigue is known and can be quantified. A statistical model of the vehicle operator's fatigue can be developed from the data from the multiple instances. In future instances, the statistical model can be applied to real-time physiological data collected from the operator during operation of the vehicle to determine a fatigue level. A warning can be provided when the statistically-calculated fatigue level exceeds a threshold level.

14 Claims, 3 Drawing Sheets

(56) References Cited

U.S. PATENT DOCUMENTS

| | | | | |
|---|---|---|---|---|
| 2008/0162088 A1* | 7/2008 | DeVaul | ............... | A61B 5/0024 |
| | | | | 702/190 |
| 2009/0040054 A1* | 2/2009 | Wang | ................. | B60W 30/095 |
| | | | | 340/576 |
| 2011/0035190 A1* | 2/2011 | DeVaul | ............... | A61B 5/0024 |
| | | | | 702/190 |
| 2012/0075122 A1 | 3/2012 | Whitlow et al. | | |
| 2013/0057671 A1* | 3/2013 | Levin | .................. | A61B 5/7221 |
| | | | | 348/78 |

OTHER PUBLICATIONS

Breidt et. al, "Robust Semantic Analysis by Synthesis of 3D Facial Motion", 2011 IEEE International Conference on Automatic Face & Gesture Recognition and Workshops (FG 2011), May 19, 2011. [Abstract Available Online] http://ieeexplore.ieee.org/abstract/document/5771336/.

Blanz et al., "Fitting a Morphable Model to 3D Scans of Faces," 2007 IEEE 11th International Conference on Computer Vision, Dec. 26, 2007. [Abstract Available Online] http://ieeexplore.ieee.org/document/4409029/.

Qin et al., "3D Deformable Face Tracking With a Commoditgy Depth Camera," 11th European Conference on Computer Vision, Part 3, Sep. 5-11, 2010, pp. 229-242 [Abstrct Available Online] http://link.springer.com/chapter/10.1007/978-3-642-15558-1_17.

Vural et al., "Drowsy Driver Detection Through Facial Movement Analysis." IEEE International Workshop, Oct. 20, 2007. [Available Online] https://www.researchgate.net/publication/221110528_Drowsy_Driver_Detection_Through_Facial_Movement_Analysis.

* cited by examiner

(12)  US 9,771,081 B2

SYSTEM FOR FATIGUE DETECTION USING A SUITE OF PHYSIOLOGICAL MEASUREMENT DEVICES

BACKGROUND

Professional vehicle operators such as airline pilots, train operators, and truck drivers can face long and irregular duty periods. As a result, such vehicle operators can become fatigued during the course of a duty period. Fatigue may result in reduced operator performance.

SUMMARY

Embodiments described herein read biometric sensor data for a vehicle operator at known and/or self-reported fatigue levels to develop a statistical model of fatigue for the vehicle operator. Later, during vehicle operation, biometric sensors located relative to the vehicle controls and/or the vehicle operator can gather biometric data about the vehicle operator. The gathered biometric data can be input to the statistical model to output an indication of fatigue level of the vehicle operator. In various embodiments, real-time data about a vehicle operator is received from a plurality of biometric sensors during operation of the vehicle. The data can be applied to a statistical model, specific to the particular vehicle operator, to calculate an indication of fatigue level of the operator. The indication of fatigue level can be output (e.g., for display to the operator or to a remote computer system).

In various embodiments, a system for monitoring fatigue of a vehicle operator in real time can include memory that stores a statistical model of fatigue for a vehicle operator. The system can also include a plurality of biometric sensors that can detect in real time different biometric data about the vehicle operator. The biometric sensors can be arranged relative to controls for the vehicle that the vehicle operator can use to control the vehicle. The system can also include a processor configured to apply the detected biometric data to the statistical model and calculate an indication of fatigue level for the vehicle operator.

In various embodiments, a computer-program product for monitoring a vehicle operator's level of fatigue can include a computer-readable medium that stores computer-readable program code. The program code can be configured to receive real-time biometric data related to a vehicle operator during operation of a vehicle. The program code can apply the data to a statistical model of fatigue, specific to the vehicle operator, to calculate an indication of fatigue level of the vehicle operator. The program code can then output the calculated indication of fatigue level of the vehicle operator.

BRIEF DESCRIPTION OF ILLUSTRATIONS

DETAILED DESCRIPTION

Figure 1:
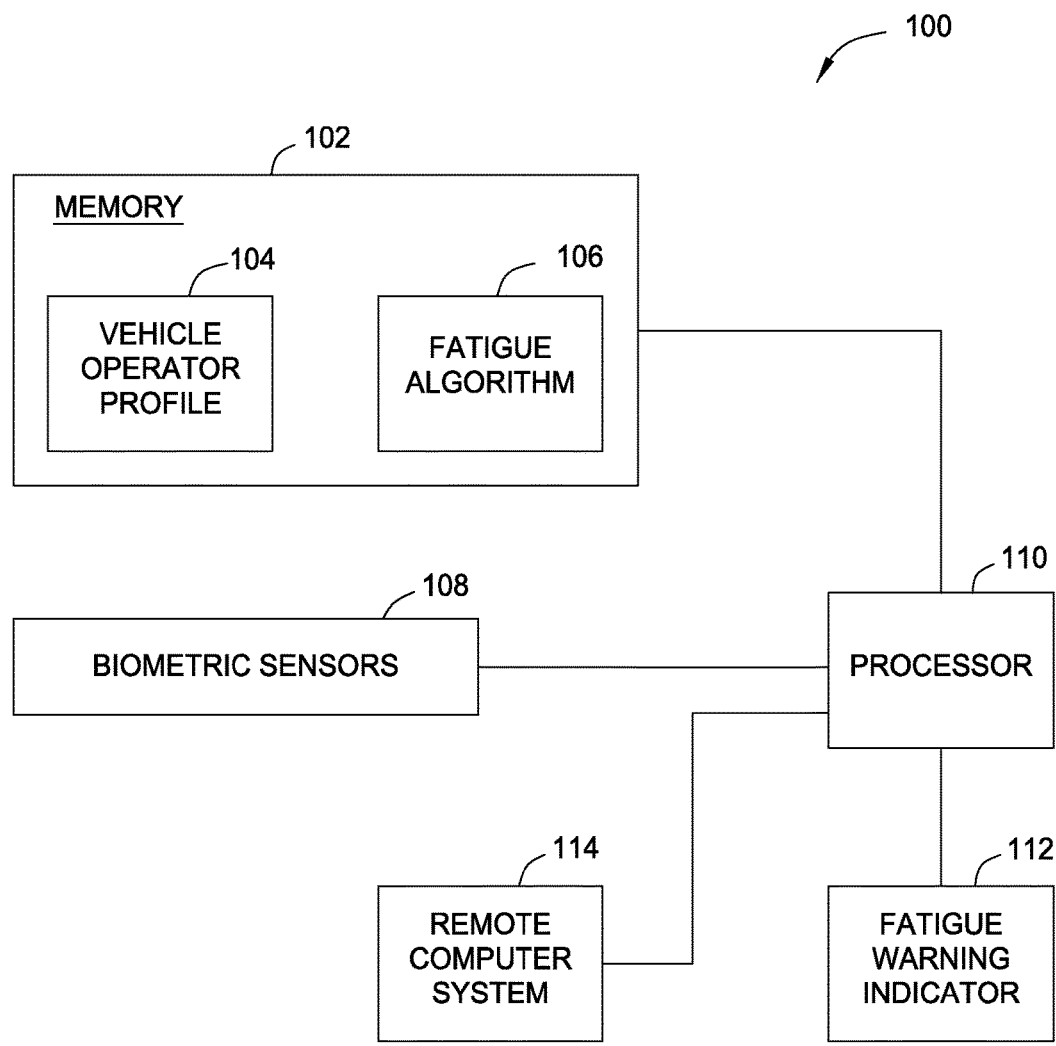
FIG. 1 illustrates a block diagram for an embodiment of a system for measuring fatigue of a vehicle operator.

Referring to FIG. 1, in various embodiments, described herein, a system 100 can use a statistical model, specific to a particular vehicle operator, to calculate an indication of fatigue level for the operator that may be represented in a signal that is sensed by the operator, another person, or a machine. As used herein an indication of fatigue level can be a unit-less quantity on an arbitrary scale that may be used to define relative levels of fatigue. For example, the indication of fatigue level of an operator can be a numeral between 0 and 1, wherein 0 is fully rested and 1 is fully fatigued. As another example, the indication of fatigue level of an operator can be a numeral between 0 and 10, wherein 0 is fully rested and 10 is fully fatigued. The system 100 can include memory 102 in communication with a processor 110 (e.g., a computer processor). The memory 102 can include a fatigue algorithm 106 (e.g., in a computer program product) that, when executed by the processor 110, performs the statistical analysis and various operations described below. The memory 102 can also store one or more vehicle operator profiles 104. Various embodiments of the system 100 can also include a remote computer system 114 that can store various statistical models of fatigue for respective vehicle operators, historical biometric data for respective vehicle operators, and/or historical statistical indicators of fatigue levels for respective vehicle operators. The remote computer system 114 can also store various statistical models of fatigue based on groups of operators having common characteristics (e.g., age, gender, experience, and body mass index). As described in greater detail below, a vehicle operator profile 104 can include a statistical model of fatigue for a particular vehicle operator, based on a plurality of different biometric information. In various embodiments, the system 100 can be personal to a particular vehicle operator. For example, the system 100, except for the remote computer system 114, described in greater detail below, may be worn by the vehicle operator, and the system 100 may move among different vehicles with the operator. In such embodiments, the memory 102 may only store the vehicle operator profile 104 for the particular vehicle operator that uses the system 100. In various other embodiments, the system 100 can be at least partially integrated in the vehicle. In such embodiments, at least portions of the system, such as the memory 102 and the processor 110 can be integrated into the vehicle. In such systems, the memory 102 can include selected vehicle operator profiles 104 for each operator, for example each operator who has operated and/or who may operate the vehicle. In various embodiments, the vehicle may be remote controlled, meaning that the vehicle operator operates the vehicle from a remote station. For example, drone aircraft may be operated from thousands of miles away by pilots seated at consoles with flight controls. In such embodiments, the system 100 can be worn by the vehicle operator and/or at least partially integrated into the console.

The system 100 can also include a plurality of biometric sensors 108 that detect behaviors and/or activities of the vehicle operator during operation of the vehicle that may be associated with fatigue. For example, the biometric sensors 108 can include one or more digital cameras that can measure facial expressions, head posture, and/or body posture of the vehicle operator. The biometric sensors 108 can also include one or more gyroscopes, solid state position sensors, or the like to measure head and/or body posture. Deviations from a vehicle operators baseline head and/or body posture, such as slouching and/or a head tilted toward the chest, may indicate fatigue. The biometric sensors 108 can also include one or more digital cameras that can detect information about the eyes of the vehicle operator. For example, the digital cameras can detect various eye metrics, such as eye blink rate (i.e., how often the vehicle operator blinks), eye movement (i.e., how much the vehicle operator is looking around rather than staring in one direction), and/or eye closure amount (e.g., how much of the vehicle operator's eyes are covered by his eye lids) of the vehicle operator. Deviations in blink rate and/or a change in blink rate from a vehicle operator's baseline measurements may indicate fatigue. Additional examples of fatigue indicators can include eyes fixing on one spot (e.g., not scanning the environment) more or less than a baseline amount and partially-closed eye lids more or less than a baseline amount. The biometric sensors 108 can also include sensors that detect electrical activity of the vehicle operator. For example, the biometric sensors 108 can include sensors to detect the heart rate of the vehicle operator by measuring electrical signals in the body that regulate heart beats. A heart rate sensor may be included in a wrist watch, chest strap, or the like. The heart rate sensor may also be incorporated into vehicle controls, such as a steering wheel and/or yoke. In various embodiments, a digital camera may be able to detect the heart rate of the vehicle operator (e.g., by monitoring pulsing of a vein in the vehicle operator's temple). Deviations in heart rates from a baseline level for a vehicle operator may indicate fatigue. The biometric sensors 108 can also include sensors to detect one or more of electroencephalography (EEG) data, electrooculography (EOG) data, electromyography (EMG) data, and electrocardiography (EKG) data of the vehicle operator. For example, the biometric sensors 108 can include a chest strap and/or a head band with various contact sensors in contact with the vehicle operator's skin. In various embodiments, the contact sensors can be incorporated into vehicle interfaces. For example, pilots often wear headsets for communicating with air traffic control, other aircraft, etc. The various contact sensors could be arranged in or on the pilot headset. The EEG, EOG, EMG, and/or EKG data can be used to determine brain activity, eye muscle movements (e.g., blinks), jaw muscle movements, heart rate and/or heart function, and the like. As described above, deviations in heart rate from a baseline level for a vehicle operator may indicate fatigue. Similarly, deviations in brain activity (e.g., voltage) from baseline levels for a vehicle operator may indicate fatigue. The biometric sensors 108 can also include a microphone to detect and observe the vehicle operator's speech. For example, a microphone in a pilot's headset or a citizen's band (CB) radio microphone that may be used by a truck driver. The microphone can also be arranged in the driving compartment (e.g., cockpit) of the vehicle. Generally, a vehicle operator may not enunciate words differently and/or may make more speaking mistakes (e.g., stuttering) when he is fatigued. Similarly, pilots often repeat an air traffic controller's instructions. The microphone may compare the pilot's response to an air traffic controller's instructions, to determine if the pilot has made any speaking mistakes. As additional biometric sensors and improvements in existing sensors are developed, they may be used in the methods and systems disclosed herein.

In embodiments in which the system is personal to a particular vehicle operator, all of the biometric sensors 108 may be worn by the operator (e.g., incorporated into clothing, headwear, jewelry, watches, eyewear, or the like). Additionally, the memory 102, processor 110, and fatigue warning indicator 112 may be worn by the operator. In embodiments in which the system is at least partially integrated into the vehicle or the vehicle operating platform, the biometric sensors 108 may be incorporated into the vehicle and/or worn by the vehicle operator. For example, in an aircraft flight deck, the pilots may wear headsets that incorporate brain activity sensors and eye tracking sensors may be incorporated into an instrument panel in the flight deck.

The memory 102 and biometric sensors 108 can be in communication with the processor 110. The processor 110 can process the gathered biometric data in the statistical fatigue model of the vehicle operator profile 104 and output an indication of fatigue level to a fatigue warning indicator 112. As discussed below in greater detail, if the numerical indication exceeds a threshold level, then the fatigue warning indicator 112 can output a warning and/or alarm to the vehicle operator. The processor 110 can also be in communication with a remote computer system 114 (e.g., a computer used by a company dispatcher). For example, the system 100 can include a wireless transceiver that communicates with the remote computer system 114 via cellular data signals, Wi-Fi signals, VHF radio signals, and/or the like. The remote computer system 114 can gather and track fatigue levels of vehicle operators for an entire fleet. For example, an airline dispatcher may monitor the fatigue levels of various pilots in real time and use the fatigue levels to determine whether a future flight assigned to a particular pilot should be reassigned to a different pilot due to increasing levels of fatigue.

Figure 2:
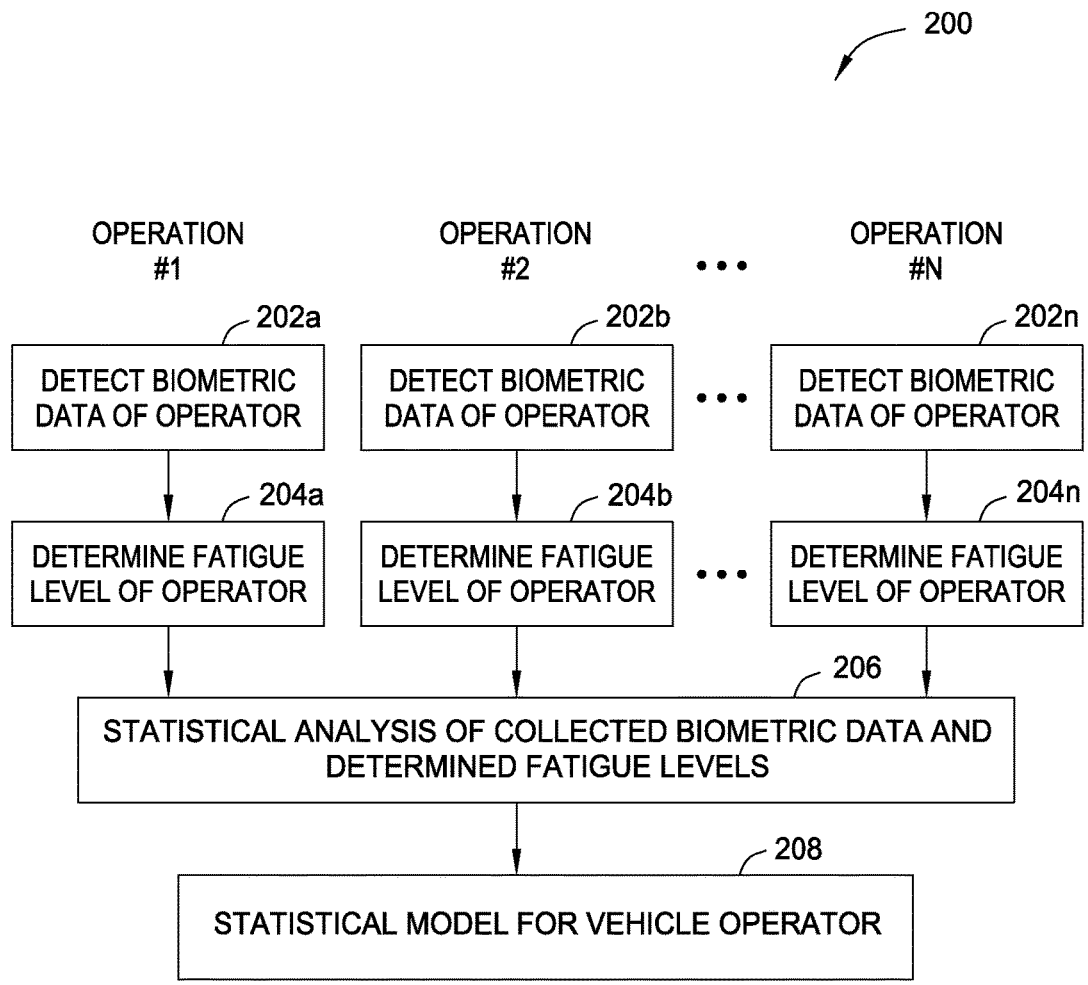
FIG. 2 illustrates a block diagram of a method for developing a statistical model for measuring fatigue of a vehicle operator.

FIG. 2 illustrates a method 200 of developing a statistical model for a vehicle operator. Each vehicle operator may demonstrate fatigue in different ways than other operators. Thus, the statistical model can be unique to each particular vehicle operator. A detailed description of the development of a statistical model is described below. Generally, according to the method 200, the various biometric sensors 108 can be read at different times when the vehicle operator's level of fatigue is known or can be determined. Each instance of readings from biometric sensors 108 and vehicle operator fatigue level can be a data point for a statistical model. A statistical analysis can be performed on the data points to create a statistical model for the operator's fatigue level as a function of the biometric data, as described further below.

As shown in FIG. 2, the data from the various biometric sensors 108 can be gathered during a plurality of instances of operation of a vehicle when the vehicle operator's fatigue level is known and/or can be quantified. Blocks 202a and 204a illustrate gathering data points from the various biometric sensors 108 and the vehicle operator's fatigue level, respectively, for a first instance. Blocks 202b and 204b illustrate gathering the data from the various biometric sensors 108 and the vehicle operator's fatigue level, respectively, for a second instance. Blocks 202n and 204n illustrate gathering the data from the various biometric sensors 108 and the vehicle operator's fatigue level, respectively, for an nth instance. One or more instances can occur during a single operation of vehicle. For example, for an airline pilot, an operation may be defined as a single flight. In various embodiments, each mission can include several instances at which biometric data and associated fatigue levels are gathered. For example, several data points may be gathered during a long-distance flight (e.g., a flight from New York City to Los Angeles). In blocks 204a-204n, the fatigue level of the vehicle operator in each instance may be determined in several different ways. In some instances, the fatigue level may be known and/or assumed. For example, a pilot flying his first mission after several days of rest may be considered to be fully rested (i.e., not fatigued). By contrast, a pilot flying his last mission at the end of his duty period may be considered to be fully fatigued. In various other instances, the fatigue level of the vehicle operator may be determined by querying the vehicle operator to rate his fatigue level (e.g., on a scale of one to ten) when biometric data is gathered (at blocks 202a-202n). Each instance in which the vehicle operator rates his fatigue level may be imprecise because the rating is subjective. For example, a vehicle operator may be queried to rate his fatigue level at three separate instances in which his fatigue level is the same. However, he may rate his fatigue level as a "four out of ten" in the first instance, a "six out of ten" in the second instance, and a "five out of ten" in the third instance. These three subjectively-rated fatigue levels average to a "five out of ten" fatigue level. As additional instances are gathered for the statistical model for a particular level of fatigue, the vehicle operator's cumulative subjective ratings of fatigue level for the particular level of fatigue may average to a number that is approximately correct. Put differently, if the vehicle operator's subjective fatigue level rating is high (relative to his actual fatigue level) as often as it is low, then an average subjective fatigue level rating may be approximately equal to the particular fatigue rating. Many statistical models that result from data points from multiple instances may inherently compensate for such subjective ratings. For example, if two instances that have identical biometric data are subjectively rated as a "four out of ten" and a "six out of ten," respectively, by the operator, then coefficients of a resulting linear regression statistical model may be the approximately equal to coefficients of the linear regression model if the operator had rated both instances as a "five out of ten." Thus, any data noise caused by subjectivity of an operator may be averaged out over a large number of instances. Data points can be gathered in an initial step to create a statistical model and additional data points can be gathered periodically to update the vehicle operator's statistical model. For example, a pilot may perform an initial series of "flights" in a flight simulator, as discussed above, to create a statistical model. Periodically, the pilot may return to the simulator to update the model (e.g., by adding new data points and/or by replacing the original data points with new data points). Additional data points can also be gathered during operation of the vehicle. For example, a pilot may be prompted to occasionally self-report his fatigue level during a flight operation, and a data point can be created from the self-reported fatigue level and the measurements from the biometric sensors 108 at the time of the pilot's self report. The new data point can be added to the data points and/or replace one or more data points that were used to generate the statistical model. For example, the new data point can be added to the existing data points. As another example, the new data point may replace a data point (e.g., the oldest data point). Thereafter, the statistical analysis, discussed below with reference to block 206, can be re-run to provide an updated statistical model. For example, over time (e.g., as an operator ages), an operator's biological measurements in response to fatigue may change. By replacing the oldest data points with newly-acquired data points, the updated statistical model may continue to accurately calculate fatigue for the operator as the operator's biological measurements in response to fatigue change. In various other instances, the fatigue level of the vehicle operator can be measured relative to other metrics, such as vehicle operator reaction time. For example, as the vehicle operator becomes more fatigued, he may take longer to respond to radio communications, prompts from the vehicle, or the like). As another example, as the vehicle operator becomes more fatigued, he may not operate the vehicle with as much precision (e.g., a pilot drifting from a landing glide path or a truck driver veering out of his travel lane). A vehicle operator may be fully fatigued when his reaction time reaches or exceeds a predetermined threshold (e.g., a threshold reaction time that may be considered unsafe). Successively faster response times may be associated with successively lower fatigue levels.

In various instances, a vehicle operator can be monitored under extreme conditions to gather biometric data and determine fatigue levels for that operator. For example, airline pilots may be monitored in a flight simulator environment. To sample a pilot over a range of fatigue levels, a pilot may begin a simulator session in a well-rested state that can be considered fully rested (i.e., not fatigued). The pilot may be monitored for a period of time that is equal to or exceeds his maximum duty time to provide biometric data at times when the pilot should be most fatigued. Additionally, the pilot may be challenged in the simulator with high-workload tasks to hasten the onset of fatigue and/or increase fatigue levels beyond that which would typically be experienced during normal vehicle operations. In the controlled environment of a simulator, aspects of the vehicle operator's performance can be measured over time. For example, when confronted with an emergency situation, a refreshed vehicle operator may respond faster and/or more accurately than a fatigued operator. If a vehicle operator's responses become too slow and/or inaccurate, then the operator may be too fatigued to continue operating the vehicle. In various embodiments, the determined fatigue level of the operator can be normalized based on the operator's measured responses becoming too slow and/or inaccurate. For example, on a scale of zero to ten, where zero is fully rested and ten is fully fatigued, an operator's fatigue level can be determined to be ten when his responses become unacceptably slow, incorrect, and/or inaccurate. For example, the operator's fatigue level can be determined to be zero when his responses are equal to his personal fastest response times. Fatigue levels between zero and ten can be determined based on the operator's response times being between his fastest time and slowest time (e.g., using a linear interpolation method). As another example, the operator's fatigue level may be determined to be ten if he fails to correctly perform a particular task and/or routine required to be performable by an operator of the vehicle. For example, pilots must be able to perform certain emergency procedures, such as properly reacting to the loss of power of an engine during takeoff. If a pilot cannot properly perform such a procedure in a simulator environment due to fatigue, then the pilot's fatigue level may be determined to be a ten.

In block 206, the gathered biometric data (from blocks 202a-n) and the determined fatigue levels (from blocks 204a-n) from the multiple operations can be statistically analyzed. For example, a linear regression analysis may be performed to determine which biometric data provide the maximum discriminatory capability between fatigue levels. As other examples, a non-linear regression analysis, a machine learning analysis, neural networks trained on known fatigue/non-fatigued instances from training data, or other statistical models can be used. In block 208, the method 200 can output the resulting statistical model for the vehicle operator to the vehicle operator profile 104. In various instances, it may be found that different statistical models provide the best predictive ability for different vehicle operators. For example, the best statistical model for a first vehicle operator may be output from a regression analysis (e.g., a linear regression analysis or a non-linear regression analysis) based on self-reported fatigue measures and the best statistical model for a second vehicle operator may be output from a classification technique such as logistic regression, support vector machines, or neural networks trained on known fatigued/non-fatigued instances from training data. These methods may optionally use the full dataset of physiological fatigue factors or some reduced-dimension dataset resulting from an application of a principal components and/or partial least squares analysis.

Figure 3A:
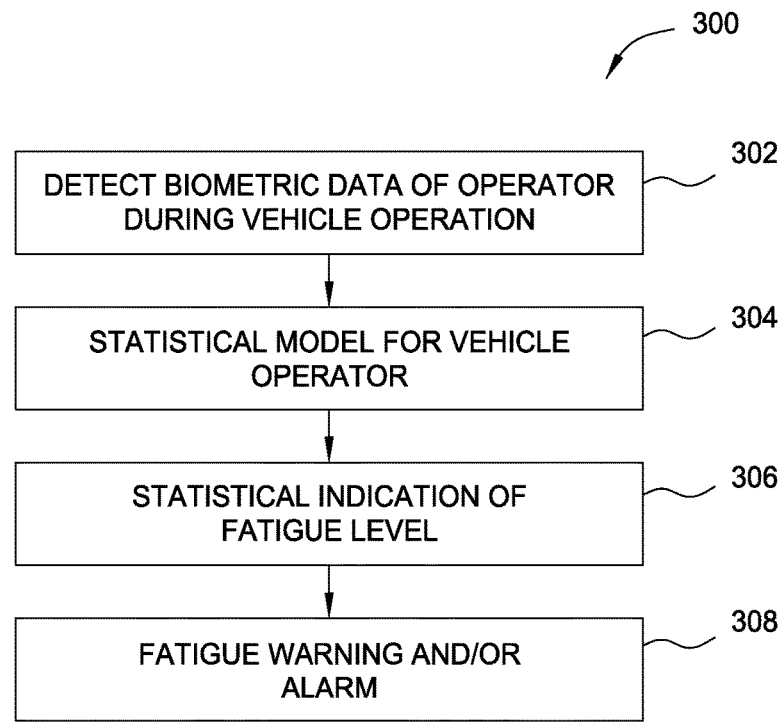
FIG. 3A illustrates a block diagram of a method for measuring fatigue of a vehicle operator.
Figure 3B:
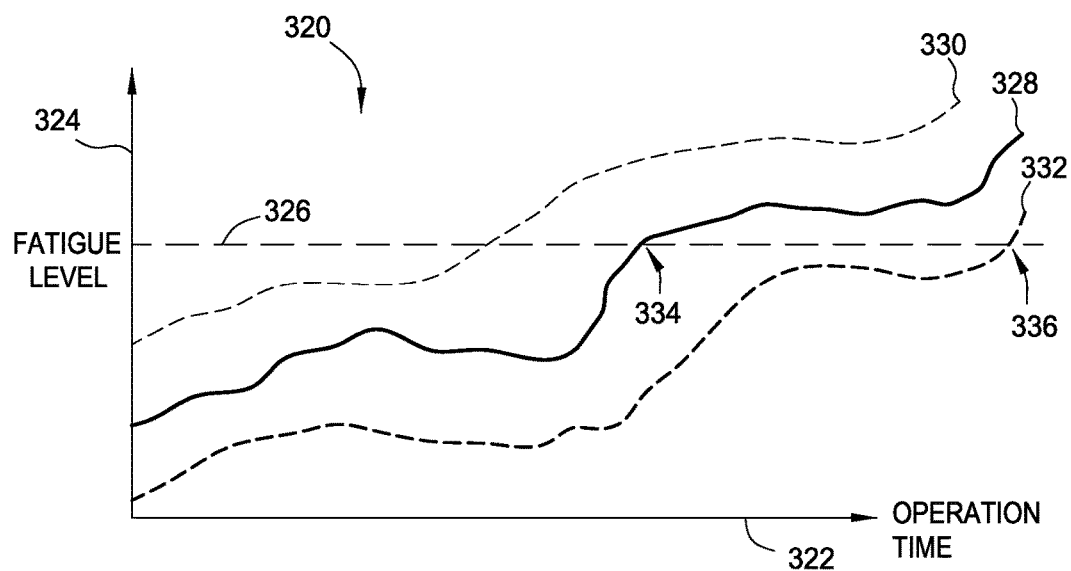
FIG. 3B is an exemplary graph of statistically-calculated fatigue of a vehicle operator over time.

Referring again to FIG. 1 and also to FIGS. 3A and 3B, the statistical model can be stored in the memory 102 for the system 100 as part of the vehicle operator profile 104. The fatigue algorithm 106 can run on the processor 110 during operation of the vehicle to perform a process 300 to determine an indication of fatigue level for the vehicle operator. FIG. 3A illustrates an exemplary process that the fatigue algorithm 106 can implement. In block 302, during vehicle operation, the processor 110 can constantly or nearly-continuously monitor the biometric sensors 108 to detect biometric data related to the vehicle operator. For example, the processor 110 may sample the biometric sensors 108 at a sufficiently high rate (e.g., once per second or once every five seconds or once per minute) to effectively provide real-time or near-real-time monitoring of the vehicle operator's fatigue level. In block 304, the processor 110 can apply the statistical model (part of the vehicle operator profile 104) to the detected biometric data. In block 306, the processor 110 can output an indication of fatigue level that results from application of the statistical model to the detected biometric data. The output indication of fatigue level can be displayed to the vehicle operator on a computer display screen. For example, in an aircraft flight deck, the indication of fatigue level can be displayed on a primary flight display, a navigation display, an engine-indicating and crew-alerting system (EICAS) display, and/or an electronic flight bag display. In a road vehicle, the indication of fatigue level can be displayed on a display screen on or proximate to the vehicle dashboard, such as a navigation display or a multipurpose display arranged relative to a speedometer. In various embodiments, the indication of fatigue level can be translated into a graphical indication of fatigue. For example, a fatigue field (e.g., an icon) on a display screen can be colored green when the indication of fatigue level is between zero and four (on a scale of one to ten), yellow when the indication of fatigue level is greater than four and less than eight, and red when the indication of fatigue level is eight or greater. As another example, a fatigue field on a display screen can include a computer generated face that looks happy when the indication of fatigue level is between zero and four (on a scale of one to ten), looks flat (i.e., neutral or calm) when the indication of fatigue level is greater than four and less than eight, and looks unhappy when the indication of fatigue level is eight or greater. In various embodiments, in block 308, the process 300 can output a first signal (e.g., a warning) and/or a second signal (e.g., an alarm) when the indication of fatigue level exceeds a threshold level. The first signal and/or the second signal can be output visually to a display screen or to a selectable-illuminated sign. The first signal and/or the second signal can also be output audibly via a speaker, klaxon, or the like.

FIG. 3B shows a chart 320 that illustrates an exemplary scenario for outputting a first and second signal regarding possible fatigue of the vehicle operator (e.g., a warning and alarm signal, respectively). The chart 320 includes a vehicle operator's duty time on the horizontal axis 322 and the indication of fatigue level of the vehicle operator on the vertical axis 324. As the vehicle operator's duty time increases, his fatigue level may also generally increase. The solid line 328 represents the indication of fatigue level calculated by the fatigue algorithm 106. The operation time on the horizontal axis can represent a vehicle operator's total duty time (e.g., a period of time with multiple flights for a pilot) or a single operation of the vehicle (e.g., a single flight). The operator's indication of fatigue level 328 may increase and/or decrease over the course of the operation time. For example, an airline pilot may get some rest between flights or in the middle of a long flight that includes a relief crew. As another example, the vehicle operator's circadian rhythm may fluctuate, resulting in natural fluctuations in the operator's fatigue level. The dashed lines above 330 and below 332 the solid lines represent the upper end and lower end, respectively, of an uncertainty interval for the statistically-calculated indication of fatigue level 328. The chart 320 also illustrates a threshold line 326. When the indication of fatigue level 328 crosses the threshold line 326 (indicated by arrow 334), the processor 110 can output a first signal (e.g., a warning) to the vehicle operator. For example, the processor 110 may output a warning that is displayed as a graphic on a computer display screen in the vehicle control area (e.g., flight deck). The warning may also include a suggested action to mitigate and/or reduce fatigue. For example, the warning can include a message (that can be played over an audio speaker or displayed on a display screen) suggesting that the vehicle operator should engage in some stretching exercises or should get a cup of coffee soon. The warning may also be output to other vehicle operators or responsible parties. For example, in an aircraft, a warning about fatigue for a first pilot could be communicated to a second pilot. Likewise, the warning could be communicated to a flight attendant on board the aircraft. The threshold level can vary from one vehicle operator to the next. Also, different operators may use different threshold levels. For example, first airline may use a threshold of eight on a scale of one to ten whereas a second airline may use a threshold of seven on the same scale.

As the indication of fatigue level 328 continues to increase, the lower end of the uncertainty interval (line 332) can also cross the threshold line (indicated by arrow 336). At this point, the processor 110 can output a second signal (e.g., an alarm) to the vehicle operator. For example, the processor 110 can output a signal that operates a klaxon, bell, chime, or the like and that also displays a message on a computer display screen. The alarm may also include a strongly-phrased instruction for the vehicle operator to cease operating the vehicle. For example, for an operator of a road vehicle, the message may instruct the vehicle operator to pull over as soon as safely possible. As another example, for an aircraft, the message may instruct the fatigued pilot to land as soon as possible or to turn control over to a non-fatigued pilot or co-pilot.

As discussed above, the indication of fatigue level, warnings, and/or alarms can also be forwarded to a remote computer system 114. In various instances, the remote computer system 114 can receive periodically-updated indication of fatigue level. For example, the processor 110 may periodically send the indication of fatigue level for a vehicle operator once every half hour (or other time interval) while the operator is operating the vehicle. The remote computer system 114 may analyze the received indications of fatigue level for trends and proactively take action to prevent a fatigued operator from continuing to operate the vehicle. For example, a remote computer system 114 may be monitoring the fatigue level of various pilots for an airline. If a particular pilot's fatigue is trending higher such that he is predicted to be unacceptably fatigued before his next-scheduled flight concludes, then the remote computer system 114 can flag the pilot's status and recommend to a scheduler that the pilot be replaced. In various embodiments, the remote computer system 114 may automatically remove the pilot from the scheduled flight and replace him with a less-fatigued pilot. In addition, the remote computer system 114 may recommend that a dispatcher intervene to prevent the vehicle operator from continuing to operate the vehicle. As an exemplary illustration, a truck driver may become fatigued and an embodiment of the system in the truck may forward an alarm to a dispatcher for the trucking company. The alarm may suggest that the dispatcher contact the truck driver via mobile phone, citizen's band (CB) radio, or the like to instruct the driver to stop for rest at the next safe stopping location (e.g., a rest stop).

By using a statistical model for fatigue, embodiments described herein can tailor fatigue detection to individual vehicle operators rather than relying on a one-size-fits-all model for all vehicle operators that may be significantly less accurate. Furthermore, by using multiple, different biometric data, embodiments described herein may reduce false positive fatigue determinations that may result from only monitoring one particular biometric reading. For example, suppose that a vehicle operator is fully refreshed at the beginning of his duty cycle and is operating his vehicle such that he is facing the rising sun. In this scenario, the vehicle operator may be squinting or partially closing his eyes because of the sun in his face. If a system for detecting fatigue based its fatigue determination solely on the amount of eye closure of the vehicle operator, then the squinting vehicle operator may be falsely flagged as being fatigued. Embodiments described herein may detect additional biometric data that can avoid such a false positive. For example, if a statistical model for the vehicle operator includes heart rate (from a heart rate monitor) and brain voltage (from an EEG sensor) in addition to eye closure, then the normal heart rate and brain voltage may offset the aberration caused by the vehicle operator squinting, and the system may not flag the operator as being fatigued.

In addition to the embodiments described above, the fatigue modeling and detection described herein can also be applied to persons who are performing monitoring tasks or other tasks that may require a high degree of vigilance. For example, embodiments can be implemented in a nuclear power plant or an air traffic control station proximal to workstations to monitor fatigue of plant operators or controllers, respectively. The fatigue modeling and detection can also be applied to tasks that are not tied to a vehicle or a workstation. For example, embodiments can be implemented in a medical environment to detect fatigue levels of doctors and/or nurses. Similarly, embodiments can be implemented in a security setting in which police, military, and/or private security personnel are guarding an area.

In various embodiments, fatigue models can be developed for different groups or classes of operators. For example, for a group of pilots, groupings may comprise different age ranges (e.g., 20-30 years of age, 31-40 years of age, 41-50 years of age, 51-60 years of age, and above 60 years of age) or other demographics. Statistical fatigue models could be generated for each age range based on data gathered from pilots within the age range. Other exemplary groupings could include gender, height, weight, and the like. A fatigue model based on a group or class of operators may be appropriate when a demographic is made of individuals who exhibit similar physiological responses to fatigue. The group-based fatigue models could be stored in a database on a remote computer system, and an appropriate model or models can be retrieved based on the demographics of the operator(s) of a vehicle. For example, if a particular aircraft flight is scheduled with a 55 year-old captain and 35 year-old first officer, then the fatigue model for the 31-40 years of age group and the fatigue model for the 51-60 years of age group can be downloaded to a fatigue monitoring system in the aircraft. The fatigue monitoring system can apply the fatigue model for the 51-60 years of age group to biometric data received from the captain to determine a numerical indication of fatigue level for the captain. The fatigue monitoring system can apply the fatigue model for the 31-40 years of age group to biometric data received from the first officer to determine a numerical indication of fatigue level for the first officer. In various embodiments, all of the statistical models for the different groups can be stored onboard the vehicle at all times. In such embodiments, the operators could identify themselves to the fatigue monitoring system as a member of a demographic or could designate the appropriate fatigue model for use.

In various instances, an operator may fall within several different fatigue models based on different groupings. For example, a fatigue monitoring system could include different fatigue models based on age groupings, gender, weight, and body mass index. Other fatigue models could be based on metrics such as blood pressure, cardiovascular health, alcohol usage, medication usage, or the like. Additional fatigue models could be based on experience level. A particular operator may fall within a first model based on age, a second model based on gender, and a third model based on weight, for example. In such an instance, the fatigue monitoring system may use the biometric data from the operator in all three fatigue models to determine three numerical indications of fatigue level for the operator. The fatigue monitoring system may average the numerical indications from the different models or ignore the lowest numerical indications, for example.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method for monitoring vehicle operator fatigue, the method comprising:

receiving a plurality of different biometric data related to a vehicle operator from a plurality of biometric sensors during real time operation of a vehicle;

calculating a fatigue level for the vehicle operator by applying the received biometric data to a statistical model of fatigue, wherein the statistical model of fatigue outputs an indication of the calculated fatigue level for the vehicle operator, wherein the statistical model of fatigue is created by:

recording biometric data about the vehicle operator from the plurality of biometric sensors during a plurality of previous operations of the vehicle, wherein each of the plurality of previous operations corresponds to a respective fatigue level of a plurality of corresponding fatigue levels of the vehicle operator relative to a predefined numerical scale, each of the plurality of corresponding fatigue levels being at least one of: known, assumed, and self-reported by the vehicle operator; and performing statistical analysis on the recorded biometric data to determine the statistical model of fatigue by ascertaining which statistical model of fatigue results in a best fit of the recorded biometric data to the plurality of corresponding fatigue levels for the plurality of previous operations.

2. The method of claim 1, wherein the received biometric data comprises at least one of:
electroencephalography (EEG) data;
electrooculography (EOG) data;
electromyography (EMG) data;
electrocardiography (EKG) data;
heart rate data;

blink rate data;
voice data;
head posture data;
body posture data;
eye movement data;
eye closure data;
body temperature data;
galvanic skin response data; and
video data.

3. The method of claim 1, further comprising, upon determining that the indication of the calculated fatigue level for the vehicle operator output by the statistical model of fatigue exceeds a threshold level of fatigue, outputting a first signal.

4. The method of claim 1, wherein the statistical model of fatigue includes an uncertainty interval for the indication of the calculated fatigue level for the vehicle operator output by the statistical model of fatigue; and further comprising:
upon the indication of the calculated fatigue level for the vehicle operator output by the statistical model of fatigue exceeding a threshold level of fatigue, outputting a first signal to the vehicle operator; and
upon a lower end of the uncertainty interval of the indication of the calculated fatigue level for the vehicle operator output by the statistical model of fatigue exceeding the threshold level of fatigue, outputting a second signal to the vehicle operator.

5. The method of claim 1, further comprising outputting the indication of the calculated fatigue level for the vehicle operator output by the statistical model of fatigue to a computer system.

6. A system for monitoring fatigue of a vehicle operator in real time, the system comprising:
a plurality of biometric sensors arranged relative to controls for a vehicle that are operated by a vehicle operator, wherein the plurality of biometric sensors detect a plurality of different biometric data for the vehicle operator in real time;
memory on board the vehicle, the memory storing executable code and a statistical model of fatigue for outputting an indication of a calculated fatigue level for the vehicle operator; and
a processor which, when programmed by the executable code, applies the detected biometric data to the statistical model of fatigue to determine the calculated fatigue level for the vehicle operator, wherein the statistical model of fatigue is created by:
recording biometric data about the vehicle operator during a plurality of previous operations of the vehicle, wherein each of the plurality of previous operations corresponds to a respective fatigue level of a plurality of corresponding fatigue levels of the vehicle operator relative to a predefined numerical scale, each of the plurality of corresponding fatigue levels being at least one of: known, assumed, and self-reported by the vehicle operator; and
performing statistical analysis on the recorded biometric data to determine the statistical model of fatigue by ascertaining which statistical model of fatigue results in a best fit of the recorded biometric data to the plurality of corresponding fatigue levels for the plurality of previous operations.

7. The system of claim 6, wherein the plurality of biometric sensors comprises at least two of:
an electroencephalography (EEG) sensor;
an electrooculography (EOG) sensor;
an electromyography (EMG) sensor;
an electrocardiography (EKG) sensor;
a heart rate sensor;
a blink rate sensor;
a voice sensor;
a head posture sensor;
a body posture sensor;
an eye movement sensor;
an eye closure sensor;
a body temperature sensor;
a galvanic skin response sensor; and
a video sensor.

8. The system of claim 6, wherein the statistical model of fatigue comprises a plurality of coefficients, based on the recorded biometric data, wherein the plurality of coefficients are set to values that result in the best fit of the recorded biometric data to the plurality of corresponding fatigue levels for the plurality of previous operations.

9. The system of claim 6, further comprising a warning indicator arranged relative to the controls and configured to display at least one warning indication; and
wherein the processor is further configured to output the at least one warning indication to the warning indicator upon determining that the indication of the calculated fatigue level for the vehicle operator output by the statistical model of fatigue exceeds a threshold level of fatigue.

10. The system of claim 6, further comprising a warning indicator arranged relative to the controls, wherein the warning indicator is configured to display a first warning indication and a second warning indication;
wherein the memory further stores an uncertainty interval for the indication of the calculated fatigue level for the vehicle operator output by the statistical model of fatigue;
wherein the processor is further configured to:
output a first warning signal to the warning indicator upon determining that the indication of the calculated fatigue level for the vehicle operator output by the statistical model of fatigue exceeds a threshold level of fatigue, wherein the warning indicator displays the first warning indication in response to the first warning signal; and
output a second warning signal to the warning indicator upon determining that a lower end of the uncertainty interval of the indication of the calculated fatigue level for the vehicle operator output by the statistical model of fatigue exceeds the threshold level of fatigue, wherein the warning indicator displays the second warning indication in response to the second warning signal.

11. The system of claim 6, further comprising a transmitter in communication with the processor, wherein the processor is configured to output the indication of the calculated fatigue level for the vehicle operator output by the statistical model of fatigue to the transmitter for transmission to a computer system.

12. A computer-program product for monitoring, in real time, vehicle operator fatigue, the computer program product comprising:
a non-transitory computer-readable medium having computer-readable program code embodied therewith, the computer-readable program code configured to:
receive a plurality of different biometric data related to a vehicle operator from a plurality of biometric sensors during real time operation of a vehicle;
calculate a fatigue level for the vehicle operator by applying the received biometric data to a statistical model of fatigue, wherein the statistical model of fatigue outputs an indication of the calculated fatigue level for the vehicle operator, wherein the statistical model of fatigue is created by:

recording biometric data about the vehicle operator from the plurality of biometric sensors during a plurality of previous operations of the vehicle, wherein each of the plurality of previous operations corresponds to a respective fatigue level of a plurality of corresponding fatigue levels of the vehicle operator relative to a predefined numerical scale, each of the plurality of corresponding fatigue levels being at least one of: known, assumed, and self-reported by the vehicle operator; and performing statistical analysis on the recorded biometric data to determine the statistical model of fatigue by ascertaining which statistical model of fatigue results in a best fit of the recorded biometric data to the plurality of corresponding fatigue levels for the plurality of previous operations.

13. The computer-program product of claim 12, further comprising computer-readable program code configured to create the statistical model of fatigue, wherein performing statistical analysis on the recorded biometric data comprises determining coefficients related to data from each of the plurality of biometric sensors that result in the best fit of the recorded biometric data to the plurality of corresponding fatigue levels for the plurality of previous operations.

14. The computer-program product of claim 13, wherein the computer-readable program code is further configured to calculate an uncertainty interval for the indication of the calculated fatigue level for the vehicle operator output by the statistical model of fatigue.

* * * * *